United States Patent
Hallgren et al.

(10) Patent No.: US 7,084,177 B2
(45) Date of Patent: *Aug. 1, 2006

(54) COMMINUTED FORM OF(S)-2-ETHOXY-3-[4-(2-{4-METHANE-SULFONYLOXYPHENYL}ETHOXY)PHENYL] PROPANOIC ACID

(75) Inventors: Agneta Hallgren, Mölndal (SE); Kristina Roos, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/148,825

(22) PCT Filed: Nov. 29, 2000

(86) PCT No.: PCT/SE00/02381

§ 371 (c)(1),
(2), (4) Date: Oct. 23, 2002

(87) PCT Pub. No.: WO01/40169

PCT Pub. Date: Jun. 7, 2001

(65) Prior Publication Data

US 2003/0069308 A1    Apr. 10, 2003

(30) Foreign Application Priority Data

Dec. 3, 1999 (SE) ................... 9904413

(51) Int. Cl.
*A61K 31/19* (2006.01)
*C07C 309/00* (2006.01)
*C07C 315/00* (2006.01)
*C07C 59/64* (2006.01)

(52) U.S. Cl. .................. 514/571; 558/44; 562/429; 562/470

(58) Field of Classification Search ............. 514/571; 562/429, 470; 558/44
See application file for complete search history.

(56) References Cited

U.S. PATENT DOCUMENTS 5,232,945 A * 8/1993 Hulin .................. 514/456
6,258,850 B1 * 7/2001 Andersson ............. 514/571
6,531,622 B1    3/2003 Boije et al.

FOREIGN PATENT DOCUMENTS

| WO | 9962871 | 12/1999 |
| WO | 9962872 | 12/1999 |

OTHER PUBLICATIONS

Alfonso, Remington's Pharmaceutical Sciences, 1990, 18th ed., p. 1306.*

* cited by examiner

*Primary Examiner*—Taylor Victor Oh
(74) *Attorney, Agent, or Firm*—White & Case LLP

(57) ABSTRACT

The present invention relates to a reduced particle size form of the compound (S)-2-ethoxy-3-[4-(2-{4-methanesulfonyloxyphenyl}ethoxy)phenyl]propanoic acid, as shown in formula (I), or a pharmaceutically acceptable salt thereof or a solvate of either thereof. The invention also concerns methods of treating one or more conditions associated with Insulin Resistance Syndrome using the reduced particle size form of the compound, or a pharmaceutically acceptable salt thereof in the manufacture of a medicament for use in one or more of said conditions. The invention further concerns pharmaceutical compositions containing the reduced particle size form of the compound, or a pharmaceutically acceptable salt thereof, or a solvate thereof, as an active ingredient, as well as processes for the manufacture of the reduced particle size form of the compound, or a pharmaceutically acceptable salt thereof.

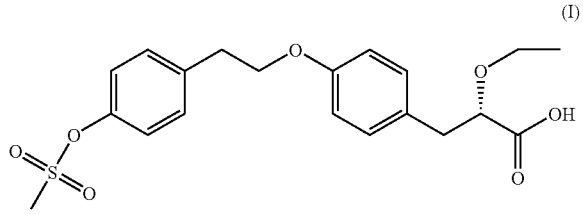

(I)

21 Claims, No Drawings

COMMINUTED FORM OF (S)-2-ETHOXY-3-[4-(2-{4-METHANE-SULFONYLOXYPHENYL}ETHOXY)PHENYL]PROPANOIC ACID

The present invention relates to a reduced particle size form of the compound (S)-2-ethoxy-3-[4-(2-{4-methanesulfonyloxyphenyl}ethoxy)phenyl]propanoic acid, as shown in the formula I below

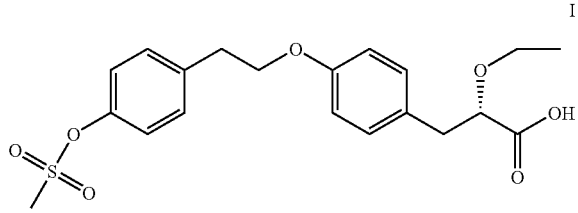

, or a pharmaceutically acceptable salt thereof or a solvate of either thereof. The invention also concerns methods of treating one or more conditions associated with Insulin Resistance Syndrome using the reduced particle size form of the compound, or a pharmaceutically acceptable salt thereof in the manufacture of a medicament for use in one or more of said conditions. The invention further concerns pharmaceutical compositions containing the reduced particle size form of the compound, or a pharmaceutically acceptable salt thereof, or a solvate thereof, as an active ingredient, as well as processes for the manufacture of the reduced particle size form of the compound, or a pharmaceutically acceptable salt thereof.

In the formulation of drug compositions, it is important for the drug substance to be in a form in which it can be conveniently handled and processed. This is of importance from the point of view of manufacture of pharmaceutical formulations comprising the active compound.

The above compound is useful in treating metabolic disorders, such as Insulin Resistance Syndrome (IRS) defined as reduced sensitivity to the actions of insulin in the whole body or individual tissues such as skeletal muscle, myocardium, fat and liver. Such conditions prevail in many individuals with or without diabetes mellitus. IRS refers to a cluster of manifestations including insulin resistance with accompanying hyperinsulinemia, possibly type II diabetes mellitus, arterial hypertension, central (visceral) obesity, dyslipidemia observed as deranged lipoprotein levels typically characterised by elevated VLDL (very low density lipoproteins) and reduced HDL (high density lipoproteins) concentrations and reduced fibrinolysis. Recent epidemiological research has documented that individuals with insulin resistance run a greatly increased risk of cardiovascular morbidity and mortality, notably suffering from myocardial infarction and stroke. In type II diabetes mellitus these atherosclerosis-related conditions cause up to 80% of all deaths.

In clinical medicine there is awareness of the need to increase the insulin sensitivity in IRS and thus to correct the dyslipidemia which is considered to cause the accelerated progress of atherosclerosis. However, this is not a universally defined disease.

We have discovered a reduced particle size form of the compound described above. This provides a basis for the present invention. Significant advantages can arise when the compound of formula I is in a reduced particle size form, for example, in the performance of the compound when it is manufactured so as to achieve uniform formulations with an even loading of active ingredient within as well between batches. In addition reductions in particle size are typically associated with increased dissolution rates when administered orally and improved oral bioavailability, when oral bioavailability is limited by the dissolution rate of the active ingredient.

Accordingly provided in the present invention is a reduced particle size form of (S)-2-ethoxy-3-[4-(2-{4-methanesulfonyloxyphenyl}ethoxy)phenyl]propanoic acid, as shown in the formula I below

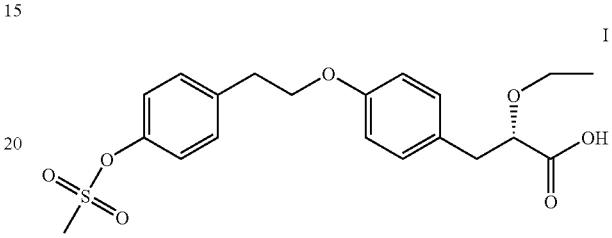

or a pharmaceutically-acceptable salt or a solvate or either thereof.

By the use of the term "reduced particle size" we refer to solid Compound 1, or a pharmaceutically-acceptable salt thereof, or a solvate of either thereof, reduced by suitable processing techniques to a solid of smaller particle size and, consequently, greater surface area. Any number of processing techniques known in the pharmaceutical field may be used to reduce solid particle size, such as grinding, milling and micronising, reference should be made to Remington: The Science and Practise of Pharmacy, 19$^{th}$ Ed., pages 1598–1602, for a more exhaustive review.

By use of the term "solvated" we include hydrated.

Accordingly presented as a further feature of the invention is a process for the preparation of a reduced particle size form of the compound of formula I, or a pharmaceutically-acceptable salt or a solvate of either thereof, comprising comminuting a solid form of the compound of formula I, or a pharmaceutically-acceptable salt or a solvate of either thereof, for a sufficient period until the desired size of particle of the compound of formula I, or a pharmaceutically-acceptable salt or a solvate of either thereof, is generated.

The range of particle sizes preferred in this invention start from, in increasing preference, moderately fine powder, fine powder, very fine powder, microfine powder to, most preferably, superfine powder.

The above references to particle sizes are taken from the British Pharmacopoeia 1993, Volume II, Appendix XVII B, A193, and are reproduced below for reference.

Moderately Fine Powder

A powder all the particles of which pass through a sieve with a nominal mesh aperture of 355 μm and not more than 40.0% by weight pass through a sieve with a nominal mesh aperture of 250 μm.

Fine Powder

A powder all the particles of which pass through a sieve with a nominal mesh aperture of 180 μm and not more than 40.0% by weight pass through a sieve with a nominal mesh aperture of 125 μm.

Very Fine Powder

A powder all the particles of which pass through a sieve with a nominal mesh aperture of 125 μm and not more than 40.0% by weight pass through a sieve with a nominal mesh aperture of 45 μm.

Microfine Powder

A powder of which not less than 90% by weight of the particles pass through a sieve with a nominal mesh aperture of 45 μm.

Superfine Powder

A powder of which not less than 90% by weight of the particles pass through a sieve with a nominal mesh aperture of 10 μm.

The particular sieves to be used in determining the particle size are described in British Pharmacopoeia 1993 Volume II, Appendix XVIIB, A193–A194, which part is incorporated herein by reference.

A feature of the invention is a reduced particle size form of a compound of formula I, as described above, for use in medical therapy.

According to a further feature of the invention there is provided a pharmaceutical composition which comprises a reduced particle size form of a compound of formula I, as described above, in association with a pharmaceutically-acceptable diluent, adjuvant or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of the reduced particle size form of a compound of formula I, as described, above that is combined with one or more excipients to produce a single dosage form will necessarily vary depending upon the host treated and the particular route of administration. For example, a formulation intended for oral administration to humans will generally contain, for example, from 0.01 mg to 50 mg of active agent compounded with an appropriate and convenient amount of excipient(s) which may vary from about 20 to about 99.99 percent by weight of the total composition. Dosage unit forms will generally contain about 0.0001 mg to about 1 mg of an active ingredient.

The invention also includes the use of a Compound of the invention, as described above in the production of a medicament for use in:

(i) treating dyslipidaemia;
(ii) treating type II diabetes mellitus;
(iii) treating hyperglycaemia;
(iv) treating hyperlipidaemia;
(v) treating hyperinsulinaemia;
(vi) treating arterial hypertension; and/or
(vii) treating abdominal obesity.

The invention also includes a method of producing an effect as defined hereinbefore or treating a disease or disorder as defined hereinbefore which comprises administering to a warm-blooded animal requiring such treatment an effective amount of a reduced particle size form of a Compound of formula I, as described above.

The size of the dose for therapeutic or prophylactic purposes of a reduced particle size form of a Compound of the invention, as described above, will naturally vary according to the nature and severity of the medical condition, the age and sex of the animal or patient being treated and the route of administration, according to well known principles of medicine. Suitable daily doses of the compounds of the invention in therapeutic treatment of humans are about 0.001–10 mg/kg body weight, preferably 0.0 1–1 mg/kg body weight.

The comminuted form of the compound of formula I may be administered as a sole therapy or they may be administered in conjunction with other pharmacologically active agents such as a anti-diabetic, anti-hypertensive, diuretic or anti-hyperlipidemic agent.

The invention will now be illustrated in the following non-limiting Examples.

EXAMPLE 1

Synthesis of (S)-2-ethoxy-3-[4-[[4-(methylsulfonyloxy)phenethyl]oxy]phenyl]propanoic acid 1-(Methylsulfonyloxy)-2-[4-(methylsulfonyloxy)phenyl]ethane 2-(4-Hydroxyphenyl)ethanol(356 g, 2.58 mol, 1.0 eq) was dissolved in methylene chloride (3500 ml) and triethyl amine (653 g, 6.44 mol, 2.5 eq). The mixture was cooled to −20° C. Methanesulfonyl chloride (657 g, 5.74 mol. 2.2 eq) was then added keeping the temperature between −25° C. and −15° C. When the conversion was >95% salts were formed which were filtered off and washed with methylene chloride (600 ml). The organic layer was washed first with saturated sodium hydrogencarbonate solution (700 ml) at 20° C. followed by water (700 ml). The methylene chloride was evaporated to dryness and the remaining residue was then used in the subsequent step.

Ethyl (S)-2-ethoxy-3-[4-[[4-(methylsulfonyloxy)phenethyl]oxy]phenyl]propanoate

Ethyl (S)-2-ethoxy-3-(4-hydroxyphenyl)-propanoate (325 g, 1.36 mol, 1.0 eq) was dissolved in acetonitrile (2600 ml). When a homogenous solution was formed, potassium carbonate (560 g, 4.05 mol, 3.0 eq) and magnesium sulfate (110 g, (0.2 g/g $K_2CO_3$)) was added. To the acetonitrile solution 1-(methylsulfonyloxy)-2-[4-(methylsulfonyloxy)phenyl]ethane (ca: 2050 ml (0.3 g/ml, 2.21 mol, 1.65 eq)) was charged and the mixture allowed to react at reflux, 82° C. for 24 hours with vigorous stirring. When a conversion >98% was reached the reaction was cooled to room temperature. The remaining salts were filtered of and washed with acetonitrile (800 ml). The filtrate was evaporated to dryness. The oil residue was then used in the subsequent step.

(S)-2-Ethoxy-3-[4-[[4-(methylsulphonyloxy)phenethyl]oxy]phenyl]propanoic acid

To the oil of ethyl (S)-2-ethoxy-3-[4-[[4-(methylsulfonyloxy)phenethyl]oxy]phenyl]propanoate (723 g(71.2% assay), 1.18 mol, 1.0 eq) was added tetrahydrofuran (THF) (3900 ml). When a homogenous solution was formed, water (900 ml) was added. The mixture was cooled to +10° C. Lithium hydroxide solution (390 ml, 4 M, 1.45 eq) was added over 1 hour. The temperature was then raised to +30° C. and the reaction allowed to proceed at this temperature for 2–3 hours. The reaction was stopped when the conversion was >99%. Ethyl acetate (500 ml) was added and the mixture cooled to room temperature. The solution was stirred for about 30 minutes and the THF was evaporated off. When about 80–90% of the THF was evaporated water (1900 ml) was added. The evaporation was continued until no THF remained in the mixture. The alkali water solution was then washed with ethyl acetate (1000 ml, 2×1250 ml, and 950 ml). The pH of the water solution of (S)-2-ethoxy-3-[4-[[4-(methylsulphonyloxy)phenethyl]oxy]phenyl]propanoic acid was then adjusted to 2.0–2.5 with HCl (aq) (550 ml, 3.0 M). Ethyl acetate (2500 ml) was added and the phases separated. The ethyl acetate solution of (S)-2-ethoxy-3-[4-[[4-(methylsulphonyloxy)phenethyl]oxy]phenyl]propanoic acid was then washed with water (700 ml) and after separation evaporated to dryness. The remaining oil was then used in the following crystallisation Crystallisation of (S)-2-ethoxy-3-[4-[[4-(methylsulfonyloxy)phenethyl]oxy]phenyl]propanoic acid The oil from 3 batches of (S)-2-Ethoxy-3-[4-[[4-(methylsulphonyloxy)phenethyl]oxy]phenyl]propanoic acid (1262 g, 3.09 mol, 1.0 eq) was dissolved in toluene (2500 ml) at 50° C. When a clear solution was achieved the solution was evaporated to decrease the amount of ethyl acetate present The volume before evaporation was 6750 ml. Another portion of toluene (2500 ml) was added, the volume after the addition being 7750 ml, and evaporation was continued. A third portion of toluene was then added to the solution, volume before the addition was 6300 ml, the volume after the addition was 8800 ml. The evaporation was continued until an opaque solution was formed, volume 8200 ml. Isooctane (1000 ml) was then added to the solution which had been heated to 40° C. The crystallisation was initiated by seeding at 40° C. The mixture was vigorously stirred until a slurry was formed. The agitation rate was then decreased. The slurry was left crystallising over night. The slurry was then filtered and washed with toluene:isooctane 5:1 (1800 ml). The crystals were then dried under reduced pressure at 40° C.

EXAMPLE 2

Preparation of Reduced Particle Size Form of Compound 1

EXAMPLE 2:1

| Compound 1 | 0.8 g |
| Hydroxypropyl cellulose LF | 24 g |
| Water | 1000 g |

Compound 1 was dispersed in 600 g water whilst stirring with a high shear mixer. Hydroxypropyl cellulose LF was added and stirring continued until the suspension was homogenous. The suspension was pumped into a ball mill, equipped with approx. 500 ml 1.0–1.5 mm glass beads, using a peristaltic pump at approx. 70 g/min. Milling was performed at 2000 rpm. The first 200 g of the milled suspension was re-charged. The mixer, vessel, hoses and millhouse were rinsed with 400 g water.

Particle size analysis was performed on the suspension before and after milling using a Coulter LS. Mean particle size was measured to 24.93 μm and 7.086 μm respectively.

EXAMPLE 2:2

| Compound 1 | 8 g |
| Hydroxypropyl cellulose LF | 24 g |
| Water | 1000 g |

Compound 1 was dispersed in 400 g water whilst stirring with a high shear mixer. Hydroxypropyl cellulose LF was added and stirring continued until the suspension was homogenous. The suspension was pumped into a ball mill, equipped with approx. 500 ml 1.0–1.5 mm glass beads, using a peristaltic pump at approx. 80 g/min. Milling was performed at 2000 rpm. The first 200 g of the milled suspension was re-charged. The mixer, vessel, hoses and millhouse were rinsed with 600 g water.

Particle size analysis was performed on the suspension before and after milling using a Coulter LS. Mean particle size was measured to 14.79 μm and 7.614 μm respectively.

EXAMPLE 2:3

| Compound 1 | 5 g |
| Hydroxypropyl cellulose LF | 600 g |
| Water | 8000 g |

Compound 1 was dispersed in 4000 g water whilst stirring with a high shear mixer. Hydroxypropyl cellulose LF was added and stirring continued until the suspension was homogenous. The suspension was pumped into a ball mill, equipped with approx. 500 ml 1.0–1.5 mm glass beads, using a peristaltic pump at approx. 75 g/min. Milling was performed at 2000 rpm. The first 200 g of the milled suspension was re-charged. The mixer, vessel, hoses and millhouse were rinsed with 4000 g water.

Particle size analysis was performed on the suspension before and after milling using a Coulter LS. Mean particle size was measured to 48.35 μm and 6.822 μm respectively.

What is claimed is:

1. A reduced particle size form of either (S)-2-ethoxy-3-[4-(2-{4-methanesulfonyloxyphenyl}ethoxy) phenyl]propanoic acid as shown in formula I below

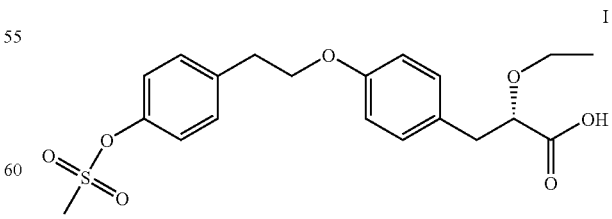

I or a pharmaceutically-acceptable salt thereof or a solvate of either which is a moderately fine powder, all the particles of which pass through a sieve with a nominal mesh aperture of 355 μm and not more than 40.0% by weight pass through a sieve with a nominal mesh aperture of 250 μm, and which form is in association with hydroxypropyl cellulose.

2. A reduced particle size form of either (S)-2-ethoxy-3-[4-(2-{4-methanesulfonyloxyphenyl}ethoxy)phenyl]propanoic acid, as shown in formula I below

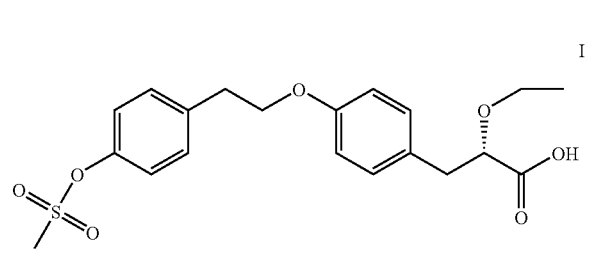

or a pharmaceutically-acceptable salt thereof or a solvate of either which is a fine powder, all the particles of which pass through a sieve with a nominal mesh aperture of 180 μm and noL more than 40.0% by weight pass through a sieve with a nominal mesh aperture of 125 μm, and which form is in association with hydroxypropyl cellulose.

3. A reduced particle size form of either (S)-2-ethoxy-3-[4-(2-{4-methanesulfonyloxyphenyl}ethoxy) phenyl]propanoic acid as shown in formula I below

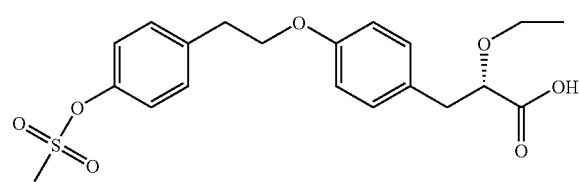

or a pharmaceutically-acceptable salt thereof or a solvate of either which is a very fine powder, all the particles of which pass through a sieve with a nominal mesh aperture of 125 μm and not more than 40.0% by weight pass through a sieve with a nominal mesh aperture of 45 μm, and which form is in association with hydroxypropyl cellulose.

4. A reduced particle size form of either (S)-2-ethoxy-3-[4-(2-{4-methanesulfonyloxyphenyl}ethoxy)phenyl]propanoic acid, as shown in formula I below

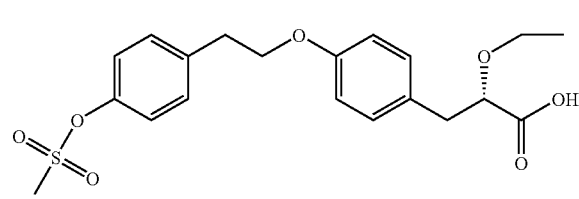

or a pharmaceutically-acceptable salt thereof or a solvate of either which is a microfine powder, of which not less than 90% by weight of the particles pass through a sieve with a nominal mesh aperture of 45 μm, and which form is in association with hydroxypropyl cellulose.

5. A reduced particle size form or either (S)-2-ethoxy-3-[4-(2-{4-methanesulfonyloxyphenyl}ethoxy)phenyl]propanoic acid, as shown in formula I below

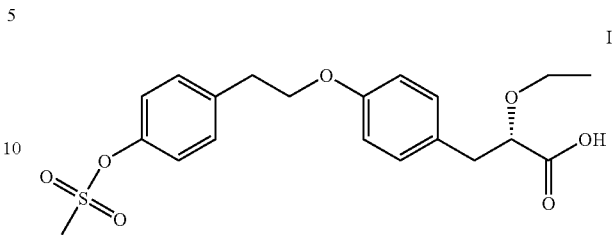

or a pharmaceutically-acceptable salt thereof or a solvate of either which is a superfine powder, of which not less than 90% by weight of the particles pass through a sieve with a nominal mesh aperture of 10 μm, and which form is in association with hydroxypropyl cellulose.

6. A process for the preparation of a reduced particle size form of the compound of formula I, or a pharmaceutically-acceptable salt or a solvate of either according to any one of claims 1 and 2–5, comprising comminuting a solid form of the compound of formula I, or a pharmaceutically-acceptable salt or a solvate of either, in the presence of hydroxypropyl cellulose for a sufficient period until the desired size of particle of the compound of formula I, or a pharmaceutically-acceptable salt or a solvate of either, is generated.

7. A reduced particle size form of either (S)-2-ethoxy-3-[4-(2-{4-methanesulfonyloxyphenyl}ethoxy)phenyl]propanoic acid, as shown in formula I below

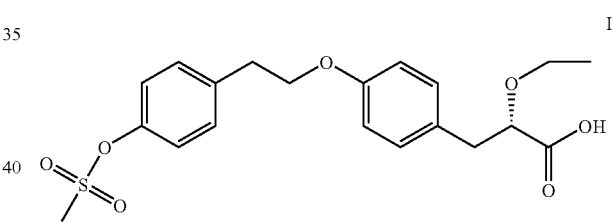

or a pharmaceutically-acceptable salt thereof or a solvate of either.

8. The reduced particle size form according to claim 7 which is a superfine powder.

9. The reduced particle size form according to claim 7 which is a microfine powder.

10. The reduced particle size form according to claim 7 which is a very fine powder.

11. A reduced particle size form of either (S)-2-ethoxy-3-[4-(2-{4-methanesulfonyloxyphenyl }ethoxy) phenyl] propanoic acid, as shown formula I below

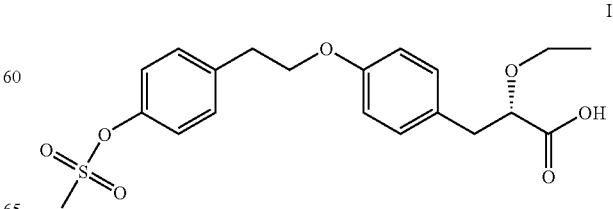

or a pharmaceutically-acceptable salt thereof or a solvate of either which is a moderately fine powder, all the particles of which pass through a sieve with a nominal mesh aperture of 355 μm and not more than 40.0% by weight pass through a sieve with a nominal mesh aperture of 250 μm.

12. A reduced particle size form of either (S)-2-ethoxy-3-[4-(2-{4-methanesulfonyloxyphenyl}ethoxy)phenyl]propanoic acid, as shown in formula I below

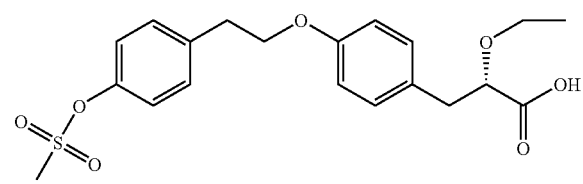

or a pharmaceutically-acceptable salt thereof or a solvate of either which is a fine powder, all the particles of which pass through a sieve with a nominal mesh aperture of 180 μm and not more than 40.0% by weight pass through a sieve with a nominal mesh aperture of 125 μm.

13. A reduced particle size form of either (S)-2-ethoxy-3-[4-(2-{4-methanesulfonyloxyphenyl}ethoxy)phenyl]propanoic acid, as shown in formula I below

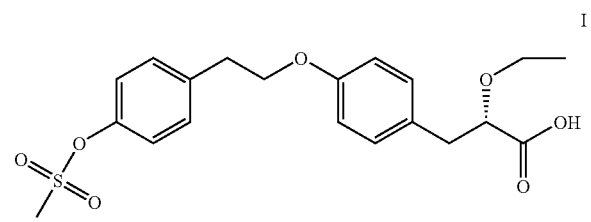

or a pharmaceutically-acceptable salt thereof or a solvate of either which is a very fine powder, all the particles of which pass through a sieve with a nominal mesh aperture of 125 μm and not more than 40.0% by weight pass through a sieve with a nominal mesh aperture of 45 μm.

14. A reduced particle size form of either (S)-2-ethoxy-3-[4-(2-{4-methanesulfonyloxyphenyl}ethoxy)phenyl]propanoic acid, as shown in formula I below

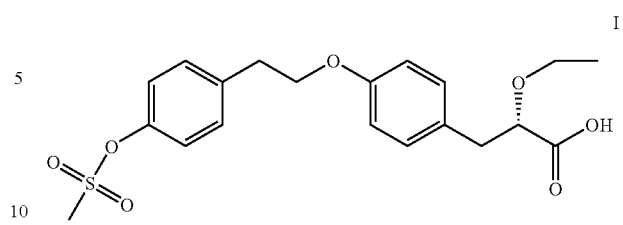

or a pharmaceutically-acceptable salt thereof or a solvate of either which is a microfine powder, of which not less than 90% by weight of the particles pass through a sieve with a nominal mesh aperture of 45 μm.

15. A reduced particle size form of either (S)-2-ethoxy-3-[4-(2-{4-methanesulfonyloxyphenyl}ethoxy)phenyl]propanoic acids as shown in formula I below

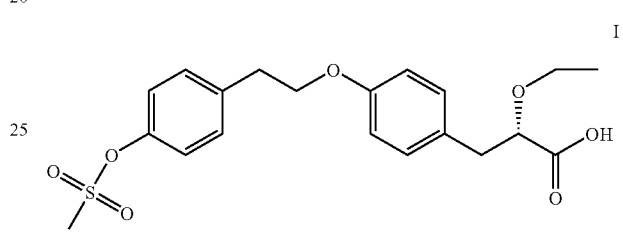

or a pharmaceutically-acceptable salt thereof or a solvate of either which is a superfine powder, of which not less than 90% by weight of the particles pass through a sieve with a nominal mesh aperture of 10 μm.

16. The reduced particle size form according to any one of claims 1, 2–5 and 7–15, wherein the compound of formula I is as the free acid.

17. A process for the preparation of a reduced particle size form of the compound of formula I, or a pharmaceutically-acceptable salt or a solvate of either according to any one of claims 7–15, comprising comminuting a solid form of the compound of formula I, or a pharmaceutically-acceptable salt or a solvate of either, for a sufficient period until the desired size of particle of the compound of formula I, or a pharmaceutically-acceptable salt or a solvate of either, is generated.

18. A pharmaceutical composition comprising a combination according to any one of claims 1 and 2–5 in the form of a tablet.

19. A pharmaceutical composition comprising a substance as defined in any one of claims 7–15 in association with a pharmaceutically-acceptable diluent, adjuvant or carrier.

20. A composition according to claim 19, wherein the composition is in the form of a tablet.

21. A pharmaceutical composition comprising a composition according to claim 16 in the form of a tablet.

* * * * *

UNITED STATES PATENT AND TRADEMARK OFFICE
CERTIFICATE OF CORRECTION

PATENT NO. : 7,084,177 B2
APPLICATION NO. : 10/148825
DATED : August 1, 2006
INVENTOR(S) : Hallgren et al.

It is certified that error appears in the above-identified patent and that said Letters Patent is hereby corrected as shown below:

Col. 6, lines 49-51:
"(S)-2-ethoxy-3-[4-(2-{4-methanesulfonyloxyphenyl}ethoxy) phenyl]propanoic acid" should read --(S)-2-ethoxy-3-[4-(2-{4-methanesulfonyloxyphenyl}ethoxy)phenyl] propanoic acid--.

Col. 7, line 22:
"noL" should read --not--.

Col. 7, lines 25-27:
"(S)-2-ethoxy-3-[4-(2-{4-methanesulfonyloxyphenyl}ethoxy) phenyl]propanoic acid" should read --(S)-2-ethoxy-3-[4-(2-{4-methanesulfonyloxyphenyl}ethoxy)phenyl] propanoic acid--.

Col. 8, line 1:
"or" should read --of--.

Signed and Sealed this

Ninth Day of January, 2007

JON W. DUDAS
*Director of the United States Patent and Trademark Office*